(12) United States Patent
Ollivier et al.

(10) Patent No.: US 7,096,071 B2
(45) Date of Patent: Aug. 22, 2006

(54) SET FOR INSTALLING AN INTRACARDIAC STIMULATION OR DEFIBRILLATION LEAD EQUIPPED WITH A SCREW

(75) Inventors: Jean-François Ollivier, Villiers-le-Bacle (FR); Frédéric Bessoule, Savigny-sur-Orge (FR)

(73) Assignee: ELA Medical S.A.S., Montrouge (FR)

( * ) Notice: Subject to any disclaimer, the term of this patent is extended or adjusted under 35 U.S.C. 154(b) by 505 days.

(21) Appl. No.: 10/353,097

(22) Filed: Jan. 27, 2003

(65) Prior Publication Data

US 2003/0167082 A1 Sep. 4, 2003

(30) Foreign Application Priority Data

Jan. 25, 2002 (FR) .................... 02 00946

(51) Int. Cl.
*A61N 1/05* (2006.01)
(52) U.S. Cl. ............... 607/126; 607/122; 607/127
(58) Field of Classification Search ............. 607/122, 607/123, 126, 127, 131
See application file for complete search history.

(56) References Cited

U.S. PATENT DOCUMENTS

| | | | | |
|---|---|---|---|---|
| 3,599,422 A | * | 8/1971 | Haueter ............... | 368/147 |
| 4,209,019 A | * | 6/1980 | Dutcher et al. ........ | 607/127 |
| 4,276,716 A | * | 7/1981 | Mabuchi ............... | 446/459 |
| 4,624,265 A | * | 11/1986 | Grassi ................ | 607/123 |
| 4,646,755 A | | 3/1987 | Kane ................. | 128/785 |
| 5,129,404 A | | 7/1992 | Spehr et al. .......... | 128/785 |
| 5,522,875 A | | 6/1996 | Gates et al. .......... | 607/127 |

FOREIGN PATENT DOCUMENTS

FR  2 724 566  3/1996

\* cited by examiner

*Primary Examiner*—Robert E. Pezzuto
*Assistant Examiner*—Eric Bertram
(74) *Attorney, Agent, or Firm*—Orrick Herrington & Sutcliffe LLP

(57) ABSTRACT

A set for installing an intracardiac lead equipped with a screw in a wall of the endocardium, particularly a stimulation or defibrillation lead. This set comprises a removable stylet (50), able to be introduced inside the sheath (12) of the lead-body and mobile in translation and rotation therein. The stylet has at its distal extremity a mechanism (56) for coupling in rotation to allow the rotation (28) of the lead-head (10). The stylet (50) includes: a central core (52, 71) carrying at its distal extremity the aforementioned coupling mechanism, and at its proximal extremity a handling body (32) for handling by the physician and a hollow tube (54) axially placed around the core. The length of the hollow tube is less than the length of the core, so that the latter emerges from the hollow tube at the proximal and distal extremities of the tube, so as to allow the rotation of the core and correlatively of the coupling mechanism, by action on the handling body, primarily without setting in rotation of the hollow tube.

7 Claims, 2 Drawing Sheets

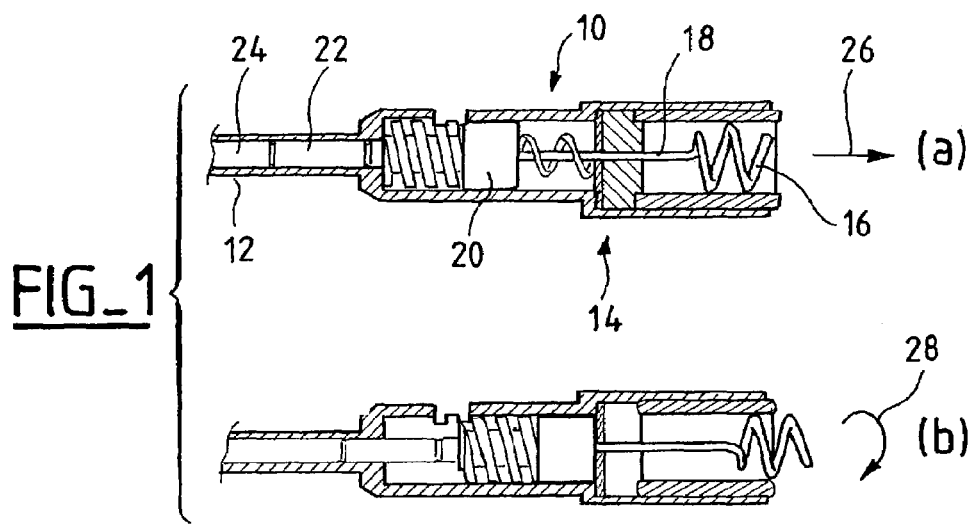
FIG_1
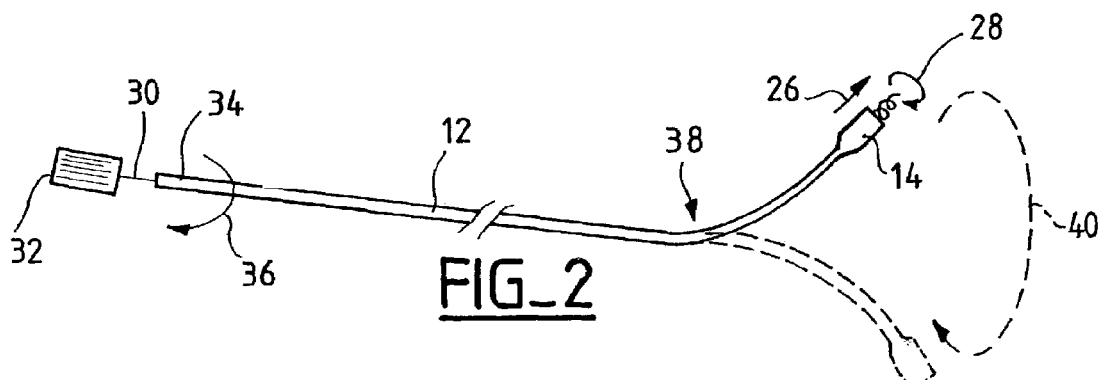
FIG_2
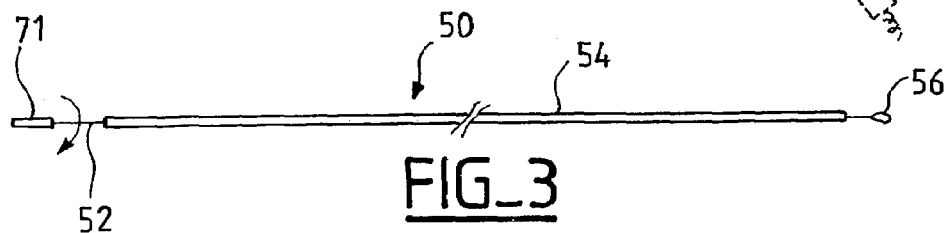
FIG_3
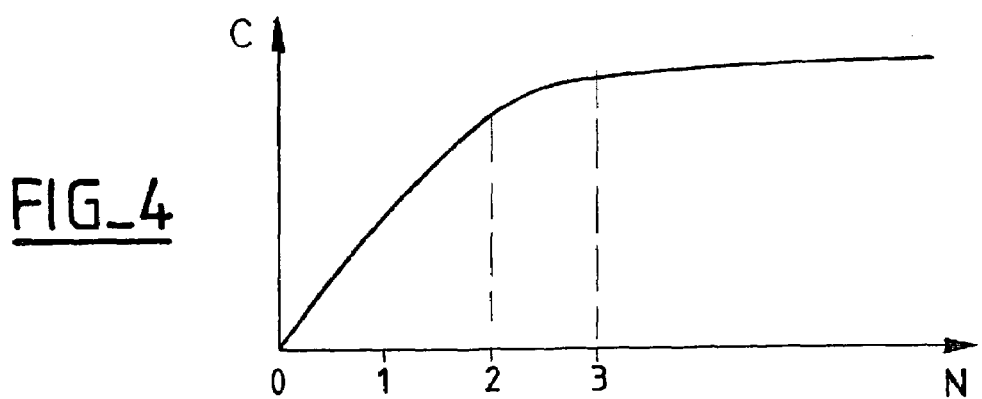
FIG_4

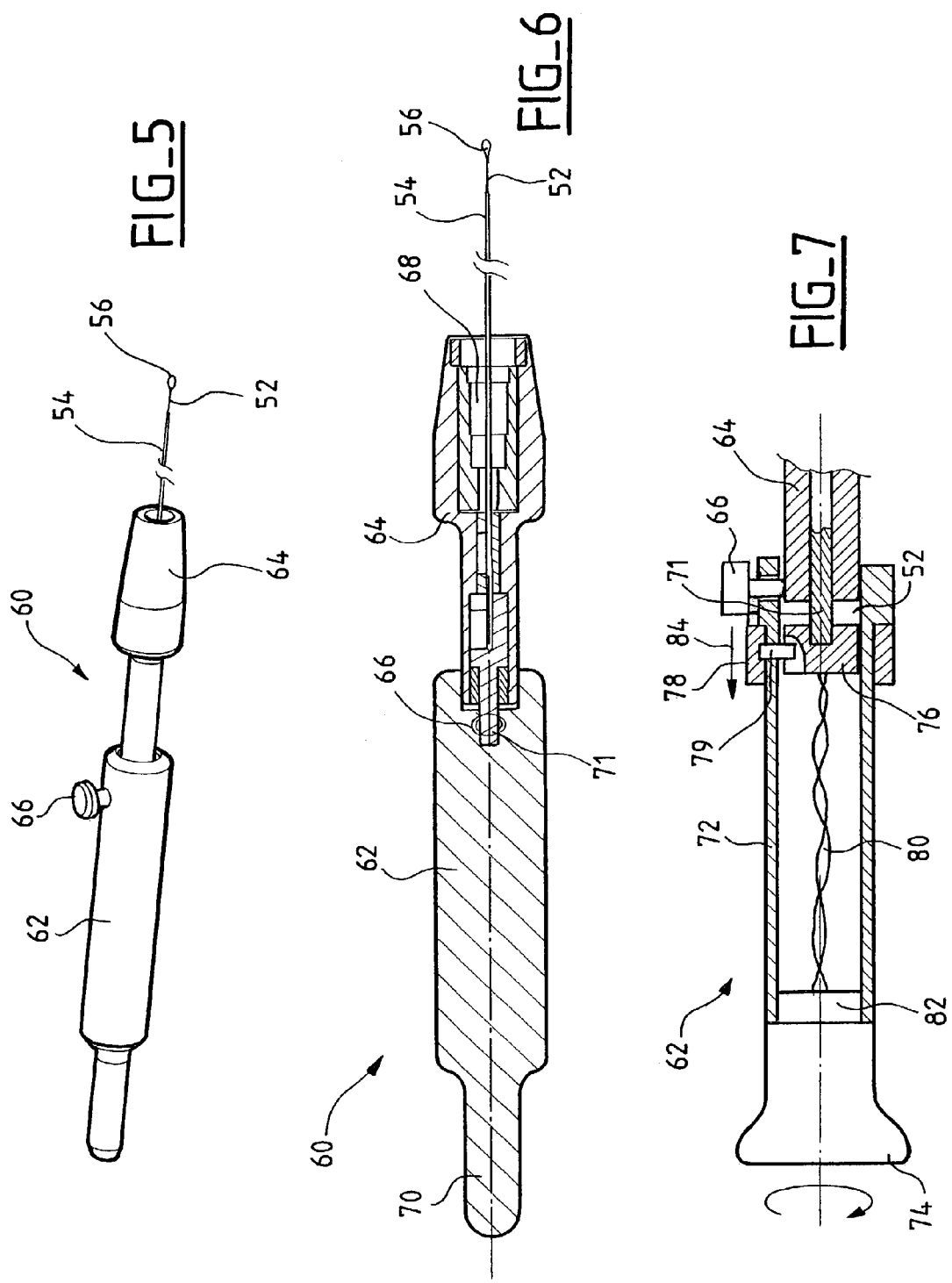

SET FOR INSTALLING AN INTRACARDIAC STIMULATION OR DEFIBRILLATION LEAD EQUIPPED WITH A SCREW

FIELD OF THE INVENTION

The present invention relates to the installation of the intracardiac leads for stimulation or defibrillation, and more particularly to the installation of the so-called "screw-in leads" (with or without a retractable screw), that are provided at their distal extremity with a screw allowing anchoring in the endocardium tissue at the contact point.

BACKGROUND OF THE INVENTION

Intercardiac leads are implanted in a cavity of the myocardium, and allow for the sensing of spontaneous depolarization signals, the application of stimulation pulses and/or a defibrillation or cardioversion shock produced by pacemaker, defibrillator, cardiovertor and/or "multisite" type device or, more generally, by an "active implantable medical device", as such devices are defined by the Jun. 20, 1990 Directive 90/385/CEE of the Council of the European Communities. EP-A-0 591 053 and its counterpart U.S. Pat. No. 5,447,534 describe such a screw-in lead, currently marketed by the assignee hereof, ELA Medical, Montrouge France, under the denomination Stelix™.

Generally, a stimulation or defibrillation lead has a "body of the lead" (called hereafter a "lead-body") formed of a sheath (i.e., a flexible hollow tube) that is finished at its distal extremity by a "lead-head" carrying the electrode or the electrodes that are intended to come in contact with the myocardium. The lead-body is equipped with an electric terminal connector at its proximal extremity for connection to a connector head of a pacemaker or defibrillator. The tube of the lead-body contains one or more wires electrically connecting the terminals of the connector to the one or more electrodes of the lead-head.

In the case of a retractable screw-in lead, the lead-head also is equipped with a mechanism making it possible to retract the screw within a housing at the distal end of the lead-head so as to protect the walls of the vein during the introduction of the lead, until the extremity of the lead-head comes into contact against the wall of the endocardium. Once this position is reached, the surgeon then manipulates the lead so as to move the screw according to a double movement. Initially there is an axial translation to deploy the screw out of the housing of the lead-head where it was during insertion, and then of rotation so that the screw will carry out its anchoring in the wall of the endocardium.

In the case of the lead described by above mentioned EP-A-0 591 053 and U.S. Pat. No. 5,447,534, this double movement of deployment and rotation is carried out in the following way.

Initially, the surgeon introduced into the hollow tube of the lead a first stylet of the "screwdriver-stylet" type, i.e., whose distal extremity presents a flattened form. This flat part comes to cooperate homologously with a receptacle within the mechanism for deployment of the screw inside the lead-body. This deployment is obtained by maintaining fixed, with one hand, the screwdriver-stylet, and turning, with the other hand, in the clockwise direction, the lead-body (by the turning proximal part of the sheath), some five to six full rotations. Once the screw is deployed, the physician withdraws the screwdriver-stylet and inserts in the tube another stylet that is equipped at its extremity with a bulge that has as a function, inside the lead-head, to make the screw interdependent with the lead-body. In contrast, in the preceding stage of deployment, these two elements were disunited (decoupled) to allow the deployment of the screw. The physician carries then out the anchoring of the screw by turning again the lead-body in the clockwise direction some five to six turns, the proximal extremity of the stylet being maintained fixed. The lead-head is provided with a system of torque limitation which minimizes the torsional stress during screwing, so as not to damage tissues and to avoid any deformation or rupture of the screw. In other words, if the resistive torque during screwing in the endocardium exceeds a given threshold, the screw is not advanced any more by the rotation of the body of lead.

This system is effective and sure. It is moreover reversible; the surgeon can unscrew the screw and retract it by reversing the installation operation as described. It presents however several disadvantages. First, it requires the use of two different stylets, which complicates the procedure because it is necessary to withdraw the screwdriver-stylet to be able to insert the stylet to be inflated (with the bulge). Second, as noted above, the deployment operation and the anchoring operation are carried out by the rotation of the lead-body (by the proximal part of the sheath), and not of the stylet. The stylet must remain fixed, its rotation being prevented by an accessory held by the surgeon. But if, instead of turning the lead-body, the surgeon turns the stylet (as that is very often the case with other types of lead), the sheath will form loops inside the cardiac cavity. This is likely to displace the lead-head, before or during the anchoring of the head, because of the elasticity of the sheath. This disadvantage is further accentuated when, for a better placement of the lead-head, the surgeon has deformed the stylet before insertion by bending it a few centimeters away from the lead-head, in order to better conform to the configuration of the cardiac cavity. In this case, any rotation, even a small one, from the stylet will tend to cause a rotation of the lead-body around the bend, instead of axially transmitting the rotation to the lead-head.

A third disadvantage is that the friction of the sheath on the wall of the vein produces during the rotational movement an accumulation of constraints that are released suddenly. It results in a jerking or jolting movement (not a smooth rotation) that is very awkward for the surgeon.

Other types of retractable screw-in leads have been proposed, for example, in U.S. Pat. Nos. 4,106,512, and 5,129,404 which also describe a device adapted for the implantation. But these devices either use a relatively complex special tool to carry out the combined movement of deployment and screwing, or work to impart a rotational movement to the sheath of the lead-body always with the risk to form loops and to displace the point of implantation before the lead-head can be anchored in the endocardium.

OBJECTS AND SUMMARY OF THE INVENTION

It is therefore, an object of the present invention to overcome the above-mentioned disadvantages, by proposing a set for installing a screw-in lead that allows, in only one movement and with a single tool, the deployment of the screw (in the case of a retractable screw) and the anchoring of the screw in the myocardium, more particularly by rotation of a handle of a stylet, and therefore without rotation of the sheath of the lead-body.

It is another object to propose such a set having a torque limitation on the screw, to minimize any damage to tissues and/or the screw, without the need to incorporate a particular torque limiting mechanism in the lead-head.

To this end, the present invention proposes a set for installing an intracardiac lead for stimulation or defibrillation of a screw-in lead type. This lead is of a type comparable with that described in above mentioned EP-A-0 591 053 and U.S. Pat. No. 5,447,534, comprising a lead-body having a flexible hollow sheath, a lead-head at a distal extremity comprising at least one electrode for stimulation and a screw for anchoring to the wall of the endocardium, the lead-head being able to be rotated to allow the anchoring of the screw by screwing in the wall of the endocardium. This set also comprises, in a manner that is in itself known, a removable stylet, able to be introduced inside the sheath of the lead-body and mobile in translation and rotation therein. The stylet has at its distal extremity a means for coupling in rotation to allow the aforementioned rotation of the lead-head.

According to the present invention, the stylet also includes: a central core carrying at its distal extremity the means for coupling in rotation, and at its proximal extremity a body to be manipulated by the physician; and a hollow tube axially placed around the central core. The length of the hollow tube is shorter than the length of the core, so that the latter emerges from the two extremities of the hollow tube, proximal and distal. This allows rotating the core and correlatively of the means for coupling in rotation, by action on the body, primarily without setting in rotation the hollow tube.

The means for coupling in rotation can preferably be a flat part formed at the extremity of the core, similar to the head of a screwdriver.

In a preferred embodiment, the material of the core is selected so that the torque likely to be transmitted by the core is higher than a minimal couple of torque exerted by any body or mechanism for handling the head on the totality of the length of the mechanism, and lower than a resistive torque opposed by the lead-head after anchoring of the screw in the wall of the endocardium. In this manner, at the end of the rotations, after a predetermined number of turns corresponding to the complete operation of deployment and screwing of the anchoring screw, any additional rotation imparted to the core results in a twisting of the core inside the tube, primarily without any increase in the couple transmitted by the means of rotation.

Preferably, the central core and the hollow tube are relatively rigid as compared to the sheath of the lead-body, and plastically locally deformable.

The body to be manipulated by the surgeon can be a handle for handling the core interdependent with the core at its proximal extremity. In an alternative, it can be envisaged to provide a handling tool comprising on the one hand a handle, forming the aforementioned body, equipped with means suitable to grip the core locally so as to rigidly connect the core with the handle, and on the other hand a handle able to be connected to the sheath of the lead-body and the hollow tube.

In a particular advantageous embodiment, the handle includes an engine means able to allow the rotation, relative to the handle, of the aforesaid means suitable to grip the core locally. A suitable engine means can in particular include an elastic spring, the handle including a winding mechanism able to put tension on the spring as well as means for limiting the torque applicable to the core during the operation of the winder.

Advantageously, the torque limiting characteristic allows in particular the set of the invention to be usable with a very large variety of screw-in leads, where the screw is or is not retractable. Yet another advantage is that the mechanism of the present invention is completely reversible, thus allowing, if necessary, a modification of the point of implantation and a withdrawing of the lead without any significant risk for the patient.

BRIEF DESCRIPTION OF THE DRAWINGS

Other benefits, characteristics and advantages of the present invention will appear to a person of ordinary skill in the art in view of the following description made with reference to the annexed drawings, in which like reference characters refer to like elements, and in which:

FIGS. 1a and 1b respectively show, in retracted position (a) and in deployed position (b), an embodiment of a lead-head of the type with a retractable screw in accordance with the present invention;

FIG. 2 illustrates the body lead in a configuration for implantation;

FIG. 3 illustrates an embodiment of stylet in accordance with the present invention;

FIG. 4 represents a torque characteristic relative to the number of revolutions during the operation of a stylet of FIG. 3;

FIGS. 5 and 6 respectively show, in perspective and in a longitudinal cross-section, a tool, for the operation of the stylet of FIG. 3; and FIG. 7 shows, in a longitudinal cross-section, an alternative embodiment of the handle of the tool of FIG. 6.

DETAILED DESCRIPTION OF THE INVENTION

With reference to FIG. 1, a lead-head 10 of the type with a retractable screw 16 is shown, with screw 16 in a retracted position (FIG. 1a) and in a deployed position (FIG. 1b).

Lead-head 10 is assembled at the extremity of a sheath 12 which together constitute a lead-body. Sheath 12 has the shape of a flexible hollow tube incorporating one or more electrical wires, as are well known, and not represented. Lead-head 10 also has a mechanism 14 making it possible to deploy a screw 16 intended to anchor itself in the wall of the endocardium, in order to ensure a mechanical, and possibly a electrical connection (according to whether or not screw 16 is insulated), with the myocardium tissue, and to prevent any displacement or dislodgment of lead-head 10.

Screw 16 is placed at the extremity of a stem 18 interdependent of a mobile piston 20 inside lead-head 10. Piston 20 is prolonged in a proximal direction by a rod 22, which can engage with and be rotated by a screwdriver-stylet introduced into the opening 24 of sheath 12.

The operation is as follows. Initially, screw 16 is deployed out of the housing of lead-head 10 where it is initially (FIG. 1a), by an axial movement, in the distal direction, compared to lead-head 10 (arrow 26, FIG. 1a). Next, (FIG. 1b), the whole of the of lead-body, thus including screw 16, is rotated (arrow 28, FIG. 1b), to perform the screwing of the deployed screw, so as to allow the anchoring of screw 16 in the wall of the endocardium (not shown). In the case of a non-retractable lead screw, only the second step corresponding to the illustration of FIG. 1b is carried out.

As described above, in the prior art technique used until now, the first step is realized by means of a screwdriver-stylet introduced the opening 24, and used to turn piston 20 relative to the sheath of lead-head 10, while the second step is carried out with a reinflated stylet, making it possible to turn the whole of the lead-body.

Referring to FIG. 2, lead-body 12 is illustrated into which a stylet 30 was introduced, stylet 30 having at its proximal extremity a handling body 32. As indicated above, in accordance with the prior art, the deployment of the screw as well as its screwing in the wall of the endocardium (movements representing arrows 26 and 28, respectively) are obtained while turning the proximal extremity 34 of lead-body sheath 12 (arrow 36, FIG. 2) by maintaining stylet 30 fixed. In other words, the surgeon holds with one hand handle 32 by immobilizing it and, with the other hand, turns the proximal extremity 34 of the lead-body. This movement is less natural than that immobilizing the proximal extremity 34 of the lead-body while turning the handle of stylet 32. However, a rotation of the stylet, even a small degree of rotation, can cause a significant displacement of the lead-head 10 when stylet 32 is made by a deformable, relatively rigid material, and was voluntarily bent (bend 38, FIG. 2) by the surgeon, in order to allow a better general orientation and to facilitate its positioning at the desired place in the cardiac cavity. Any rotation of stylet 30, even a small one, will then cause to rotate (arrow 40) the part of the lead located distally of bend 38, thus risking a dislodgement of the lead during its installation.

The invention thus proposes an improved installation technique, using only one stylet of the "screwdriver-stylet" type, but not presenting the above noted disadvantages. The stylet of the present invention is usable with any type of lead in which the deployment of the screw and screwing can be controlled by a single rotational movement, obtained by means of a screwdriver-stylet, i.e., equipped with an extremity in the shape of flat part similar to a screwdriver.

One embodiment of a stylet 50 according to the invention is illustrated with reference to FIG. 3. Stylet 50 is made of two coaxial elements, with a central core 52 placed in a hollow tube 54. The external diameter of tube 54 is comparable with that of a traditional stylet formed of a simple massive wire, for example, of a diameter of 1 French (0.33 mm). Therefore it has a diameter compatible with the internal diameter of the opening of the sheath, without modification. Central core 52 presents a length longer than that of hollow tube 50, so as to emerge at the both extremities. On the proximal side, core 52 is finished by a welded tube 71 of larger diameter, to allow an easier handling. The distal extremity of core 52 carries a flat part 56 which will allow a coupling to a body homologous (e.g., a slit or analogue) with the lead-head to allow the anchoring screw operation.

To carry out the installation operation, the surgeon introduces stylet 50 into the opening 24 of sheath 12 of the lead-body, and operates the screw 16 by rotation of central core 52—only, without rotation of external tube 54. Hollow core 52 and tube 54 can be produced in a plastically deformable material, so that the surgeon can bend the sheath-stylet unit before its introduction into the venous network. During its advance in this venous network, the device is rectified (straightened) because of the elasticity of materials, but once bend 38 reaches the cardiac cavity, it is reformed, thus making it possible for the surgeon to better position the electrode at the desired place in the cavity. Insofar as the operation of screw 16 is obtained by the rotation of central core 52 without rotation of hollow tube 54, the presence of an elbow (bend 38) is not awkward, in any way, since the lead-body is not in any way pulled by the central core, because of interposition of the hollow tube 54.

The free rotation of core 52 in hollow tube 54 is ensured by a choice of dimensions of the internal and external diameters, as well as by the state of the surface of material. One avoids in this regard the effect of friction of the stylet in the tube, which avoids the jolts of rotation.

Another advantage of the invention lies in the possibility of having a torque limitation function, without it being necessary to envisage a specific mechanism in the lead-head. Indeed, insofar as the torque is transmitted by central core 52, whose diameter is very small, as soon as the resistive torque on screw 16 exceeds the maximum torque of central core 52, no additional couple can be transmitted; it will be absorbed by core 52 which will then be twisted inside hollow tube 54.

FIG. 4 illustrates the characteristic of the couple C according to the number of revolutions N imparted to central core 52. From zero to 2 or 3 turns, corresponding to a complete deployment and screwing movement of screw 16, the couple increases gradually. When the screw is completely anchored in the myocardium, even if the surgeon continues his rotational movement, the central core twist itself inside the hollow tube, thus limiting the couple applied to the screw, thereby avoiding any rupture or torsion of the screw and any damage of the myocardium tissues. In addition, the elastic deformation limit of the material constituting the central core is selected so that, if the rotation is continued, the core is twisted in a deformation movement, typically over several tens of turns, without rupturing. This makes it possible to preserve a complete reversibility, such that a rotation in the contrary direction of the central core will authorize the unscrewing and the retraction of the screw inside the lead-head.

The rotational movement can be transmitted to the central core in various ways. One way is by a simple, traditional tool, similar to a wrench actuating by homologous sides a handle interdependent of the central core. Alternately, a specific tool, for example, that illustrated on FIGS. 5, 6 and 7, could be used.

Tool 60 (FIG. 5) comprises two mobile components in axial rotation one relative to the other, namely a handle 62 intended to rotate central core 52, and a handle 64 intended to maintain fixed hollow tube 54. A latch-tightening (set) screw 66 makes it possible to connect securely handle 62 to the extremity 71 of the central core emerging in proximal direction. Handle 64 comprises a cavity 68 shaped to receive the terminal connector present at the proximal extremity of the lead-body. This connector is press-fitted in cavity 68 so that handle 64 allows the rotation of the lead-body and the handling of hollow tube 54. By light movement of handle 64, if the stylet is bent, the surgeon can proceed to a "mapping" and a search for the optimal position of the lead under X-ray monitoring by directing the bent end towards the required position. Once this position found, handle 62 is turned, advantageously by the narrowed extremity 70 which can be easily handled between the thumb and forefinger, so as to deploy the screw (in the case of a retractable screw) and to screw the latter in the wall of the endocardium.

Handle 64 can be advantageously equipped with electrical contacts ensuring a connection with the terminals of the connector introduced into cavity 68. This will allow taking a certain number of electrical measurements before the implantation or during the course of implantation, for example, measurements of impedance or capture threshold. A second electrical contact can be established for a connection on element 71 via element 66.

In an alternative embodiment illustrated in FIG. 7, handle 62 is provided with engine means making it possible to rotate automatically and quickly central core 52 of the stylet. For this purpose, handle 62 has a fixed body 72 finished at its proximal extremity by a tip 74 forming a winder (i.e., a knob that rotates as a winding mechanism or crank), and at its distal extremity by a connector 76 interdependent of an external ring 78. A radial cylinder 79 engaged in connector 76 prevents the rotation of connector 76 and, consequently, of element 71 and thus of core 52.

A means forming a torsion spring, for example, an elastic ribbon 80 (such as a "rubber band"), connects winder 74 to connector 76. The spring 80 is put in tension, either at the factory or by the surgeon, before implantation or localization of the lead. This is carried out by turning winder 74, which causes the elastic ribbon 80 to twist and to put it under torsional stress.

To avoid any risk of damage in the event of excessive rotation of winder 74, it is envisaged to have a torque limitation mechanism 82 interposed between body 72 and winder 74. A suitable torque limiting mechanism is, for example, a mechanism of the same type as that associated with a crown of watch, as are known in the watch industry. In the event of rotation beyond a certain number of revolutions, winder 74 disunites body 72, while remaining in tension, and the surgeon perceives that it reached this point by the perception of a jump out of a pawl of this mechanism. Once the lead-head is positioned at the desired place, the surgeon moves ring 78 back a few millimeters (arrow 84); the radial cylinder 79 is then released then from the connector 76, which releases ribbon 80 and starts the rotation of element 71 and, consequently, of central core 52. This fast rotational movement for several turns is particularly advantageous because it allows a fast and effective anchoring screw, without risk of dislodging in the course of screwing. Suitable leads for implementing the invention are leads sold under the trade name STELIX™, by Ela Medical.

One skilled in the art will appreciate that the present invention can be practiced by other than the described embodiments, which are presented for the purposes of illustration and not of limitation.

We claim:

1. A set for installing an intracardiac lead of the "screw-in lead" type into a wall of the endocardium, comprising:
    a lead-body having a flexible hollow sheath, a distal extremity and a proximal extremity, a lead-head at the distal extremity, the lead-head comprising at least one stimulating electrode and a screw, the lead-head being rotatable to allow anchoring said screw into a wall of the endocardium: and
    a removable stylet sized to be introduced inside said sheath and mobile in translation and rotation inside said sheath, said stylet having a distal extremity; a means for coupling in rotation, located at said stylet distal extremity, to allow said rotation of the lead-head; a central core having a first length, a distal extremity and a proximal extremity, said means for coupling in rotation being sized to couple to said core distal extremity; a handling body coupled to said core proximal extremity; and a hollow tube axially placed around the core, said hollow tube having a second length that is shorter than said core first length, so that said central core emerges from the hollow tube at digital and proximal extremities of the tube, so as to allow the rotation of the core and correlatively the means for coupling, by action on the handling body, primarily without setting in rotation of the hollow tube,
    wherein said central core comprises a material selected so that any torque likely to be transmitted by the core is higher than a minimal torque of rotation associated with a rotation of said lead-head, and lower than a resistive torque associated with the lead-head being anchored in the wall of the endocardium, whereby, after a predetermined number of turns corresponding to a complete operation of deployment and screwing of the screw, any additional rotation of the core results in a twist of the core inside the tube, primarily without increase in the couple transmitted by means for coupling in rotation.

2. The set of claim 1, wherein the means for coupling in rotation is a flat part formed at the distal extremity of the core.

3. The set of claim 1, wherein the central core and the hollow tube are relatively rigid compared to the sheath of the lead-body, and locally plastically deformable.

4. The set of claim 1, in which the handling body further comprises a handle interdependent of the core at its proximal extremity.

5. The set of claim 1, further comprising a handling tool comprising a first handle, said first handle forming said handling body and means for gripping locally the core to connect said core to the first handle, and a second handle able to be connected to the sheath of the lead-body and the hollow tube.

6. The set of claim 5, wherein the first handle includes an engine means for rotation, relative to the second handle, of said gripping means.

7. The set of claim 6, wherein the engine means comprises an elastic spring, the first handle comprising a winder to put in tension said elastic spring, andmeans for limiting the torque applicable to the core during operation of the winder.

* * * * *